United States Patent [19]

Bosslet et al.

[11] Patent Number: 5,730,981
[45] Date of Patent: Mar. 24, 1998

[54] MONOCLONAL ANTI-GANGLIOSIDE ANTIBODY AND ITS PREPARATION

[75] Inventors: Klaus Bosslet, Marburg; Gerhard Seemann, Marburg-Elnhausen; Wolfgang Dippold, Mainz, all of Germany

[73] Assignee: Behringwerke Aktiengesellschaft, D-35001 Marburg, Germany

[21] Appl. No.: 326,362

[22] Filed: Oct. 20, 1994

Related U.S. Application Data

[63] Continuation of Ser. No. 32,863, Mar. 17, 1993, abandoned.

[30] Foreign Application Priority Data

Mar. 19, 1992 [DE] Germany ............... 42 087 795.3

[51] Int. Cl.$^6$ ............... A61K 39/395; A61K 39/44; C07K 16/30; C12N 5/12
[52] U.S. Cl. ............... 424/155.1; 424/1.49; 424/138.1; 424/174.1; 435/70.11; 435/172.2; 435/329; 435/330; 435/344; 435/344.1; 530/387.7; 530/388.85
[58] Field of Search ............... 530/387.3, 387.5, 530/388.8, 387.7, 388.85; 435/240.26, 326, 329, 330, 374, 344.1, 70.21, 172.2; 424/130.1, 141.1, 138.1, 155.1, 174.1, 1.49

[56] References Cited

U.S. PATENT DOCUMENTS

5,055,559  10/1991  Hellstrom et al. ............... 530/387

FOREIGN PATENT DOCUMENTS

| 0 189 849 | 8/1986 | European Pat. Off. . |
| 0 234 122 | 9/1987 | European Pat. Off. . |
| 0 316 882 | 5/1989 | European Pat. Off. . |
| 0 351 731 | 1/1990 | European Pat. Off. . |
| 0460607 | 11/1991 | European Pat. Off. ........ C12P 21/08 |
| 0 493 686 | 7/1992 | European Pat. Off. . |

OTHER PUBLICATIONS

Hastings et al Cancer Research 52:1681–1686 1992.
Hakomuri Ann Rev Immunol 2:103–126 1984.
Sonnino et al In: Molecular Immunology of Complex Carbohydrate eds A.M. Wv & L.G. Ams Plenum Prero NY pp. 437–464 1988.
Certified Translation of German Patent No. P 4208795.3.
Riechmann et al. Nature 332:323–327 1988.
Dippold, W., et al., "Inhibition of Human Melanoma Cell Growth in Vitro by Monoclonal Anti–$G_{D3}$–Ganglioside Antibody," *Cancer Res.*, 44:806–810 (Feb. 1984).
Yamamoto, H., et al., "Tetrasialoganglioside GQ1b Reactive Monoclonal Antibodies: Their Characterization and Application for Quantification of GQ1b in Some Cell Lines of Neuronal and Adrenal Origin(s)," *J. of Neurochemistry*, 54(7):513–577 (Feb. 1990).

Ozawa, H., et al., "Generation of one set of monoclonal antibodies specific for b–pathway ganglio–series gangliosides," *Biochimica et Biophysica Acta*, 1123(2):184–190 (Jan. 24, 1992).
Dippold, W., et al., "Immunorecognition of Ganglioside Epitopes: Correlation between Affinity and Cytotoxicity of Ganglioside Antibodies," *Eur. J. Cancer*, 28A(10):1605–1610 (Mar. 31, 1992).
Ohta, S., et al., "Antitumor effects of a novel monoclonal antibody with high binding affinity to ganglioside GD3," *Cancer Immunol. Immunother.*, 36:260–266 (1993).
Immunohistochemical Localization of Ganglioside $G_{D3}$ in Human Malignant Melanoma, Epithelial Tumors, and Normal Tissues, Dippold et al., Cancer Research, 45:3699–3705 (1985).
Cell Surface Antigens of Human Malignant Melanoma: Definition of Six Antigenic Systems With Mouse Monoclonal Antibodies, Dippold et al., Proc. Natl. Acad. Sci., 77(10):6114–6118 (1980).
Humanization of Monoclonal Antibodies, D. Güssow et al., Methods of Enzymology, 203:99–121 (1991).
Cloning Immunoglobulin Variable Domains For Expression by the Polymerase Chain Reaction, Orlandi et al., Proc. Natl. Acad. Sci., 86:3833–3837 (1989).
A Monosialoganglioside Is a Monoclonal Antibody–Defined Antigen of Colon Carcinoma, Magnani et al., Science, 212:55–56 (1982).
DNA Sequencing With Chain–Terminating Inhibitors, Sanger et al., 74(12):5463–5467 (1977).
Design and Syntheses of a Mimetic From an Antibody Complementarity–Determining Region, Saragovi et al., Science, 253:792–795 (1991).
A Novel Approach To Tc–99m–Labeled Monoclonal Antibodies, Schwarz et al., J. Nucl. Med., 28:721 (1991).
Immune and Nonimmune Effector Functions of IgG3 Mouse Monoclonal Antibody R24 Detecting the Disialoganglioside GD3 on The Surface of Melanoma Cells, Welt et al., Clin. Immunol. Immunopathol., 45:214–229 (1987).
Isolation of Overproducing Recombinant Mammalian Cell Lines By a Fast and Simple Selection Procedure, Wirth et al., Gene, 73:419–426 (1988).
Chromatographic Separation of Human Brain Gangliosides, Svennerholm, J. Neurochem., 10:613–623 (1963).

*Primary Examiner*—Lila Feisee
*Assistant Examiner*—Phillip Gambel
*Attorney, Agent, or Firm*—Finnegan, Henderson, Farabow, Garrett & Dunner, L.L.P.

[57] ABSTRACT

The invention relates to monoclonal antibodies of high avidity, which react specifically with the gangliosides GD3 and GQ1b, and to their use for detecting melanomas and other tumors or tissues expressing GD3 and GQ1b.

8 Claims, No Drawings

MONOCLONAL ANTI-GANGLIOSIDE ANTIBODY AND ITS PREPARATION

This application is a continuation of application Ser. No. 08/032,863 filed Mar. 17, 1993, now abandoned.

Murine monoclonal antibodies (MAbs) which are specific for tumor-associated antigens are used both for tumor marker tests in in vitro diagnostic investigation and for immunoscintigraphy in in vivo diagnosis. Despite many attempts to achieve tumor therapeutic effects with MAbs, the clinicotherapeutic findings have in many cases not been statistically significant. Reasons for these failures lie in the inadequate penetration of the tumors by the MAbs, their immunogenicity and their low cytotoxic potential and their cross-reactivity with certain normal tissues.

The inadequate penetration of human tumors can be overcome by the repeated long-term administration of high doses of MAbs. However, this is only possible if the MAbs have low immunogenicity. Such molecules of low immunogenicity can be prepared by humanization (Güssow, D., Seemann G., Methods in Enzymology, vol. 203, 1991) of MAbs (huMAbs). If they are provided with a corresponding Fc moiety, huMAbs possess greater cytotoxic potential. If, in addition, the MAb still possesses high tumor specificity and high affinity, it should be possible to develop a highly effective tumor therapeutic agent.

In attempting to prepare high-affinity MAbs against gangliosides, we observed that the MAbs generally possessed low affinity and cross-reacted significantly with relevant normal human tissues. Surprisingly, however, we succeeded in preparing a MAb of high avidity which reacts with the gangliosides GD3 and GQ1b and, even at low molar concentrations, displays high cytotoxic activity on melanoma cells, but shows minimal cross-reactivity with normal human tissues. The gangliosides GD3 and GQ1b are gangliosides which are closely related structurally. In accordance with the Budapest Treaty, the hybridoma 2121, which secretes the MAb BW 2121, was deposited on Mar. 5, 1992 with the DSM—German Collection of Microorganisms and Cell Cultures, Mascheroder Weg 1 B, 3300 Braunschweig, Germany, under deposition member accession number DSM ACC 2036.

The hybridoma 2121 can be prepared as follows:

Immunocompetent meals, such as, for example, the mouse, rat or sheep, are immunized with immunogen containing GD3 and/or GQ1b, for example melanoma cells or extracts thereof, the immune cells are immortalized by fusion with myeloma cells, and the hybridoma clones which arise are tested for secretion of MAbs specific for GD3 and GQ1b. Alternatively, a gene bank containing the genes coding for the variable regions of the antibodies can be prepared by recombinant DNA methods from the immune cells of immunized meals, and the clones with the desired MAb specificity can then be isolated and cloned from this gene bank using, for example, phage screening techniques.

The invention therefore relates to:

The hybridoma 2121 (DSM ACC 2036)

A monoclonal antibody (BW 2121) which is derived from the hybridoma 2121.

Monoclonal antibodies or parts thereof which bind to an epitope which is recognized by a monoclonal antibody from hybridoma 2121.

The invention further relates to monoclonal antibodies or parts thereof which are of a chimeric, humanized, bi-specific or oligospecific nature.

Humanized antibodies are particularly preferred examples thereof.

The invention additionally relates to a process for preparing the antibodies according to the invention, processes for detecting melanomas and other tumors or tissues expressing GD3 and GQ1b by the use of the antibodies according to the invention and a corresponding pharmaceutical composition or a diagnostic agent.

The MAb BW 2121 can also be defined by the following 7 features:

1) The MAb reacts in the ELISA and Magnani ITLC test (Magnani, J. L., Brockhaus, M., Smith, D. F., Ginsburg, V., Science 212: 55–57, 1982) with gangliosides which, according to the nomenclature of Svennerholm (J. Neurochem. 10: 613–623, 1963), are designated as GD3 and GQ1b. It does not bind to GD1b, GD2, GT1b, GD1a, GM1, GM2 and GM3.

2) On the basis of immunohistochemical staining of a series of 10 cryopreserved primary melanoma tumors (Dippold, W. G., Dienes, H. P., Knuth, A., Meyer zum Büschenfelde, K.-H., Cancer Res. 45: 3699–3705, 1985), the MAb BW 2121 binds homogeneously to 6 out of 10 tumors, i.e. >90% of the melanoma cells are uniformly stained; 3 of the 10 tumors react less strongly, i.e. 10–50% of the melanoma cells show a clear positive reaction. 1 of the 10 primary melanoma tumors did not react with the MAb.

A similar reaction profile, although considerably more heterogeneous, is seen in the case of the 14 melanoma metastases which have been examined. In this case the MAb BW 2121 reacts with >90% of the tumor cells in 6 of the 14 tumors. Between 5 and 50% of the tumor cells were positive in 5 of the 14 metastases, while 3 metastases showed no reaction whatsoever.

3) An immunohistochemical investigation of nevocytic nevi gave the following results:

MAb BW 2121 reacted with 3 out of 4 junctional nevi, 13 out of 14 compound nevi, 3 out of 5 dermal nevi, 8 out of 11 dysplastic nevi and 1 out of 1 congenital nevi.

4) An immunohistochemical investigation of cryopreserved normal human tissues gave the following result:

In 3 skin samples that were investigated, the basal-cell layer, the prickle-cell layer and the melanocytes were all completely negative.

Of the endocrine organs that were investigated, neither the cortex nor the medulla of 2 adrenal glands that were investigated showed any reaction. Additionally, 2 samples of Goormaghtigh cells, 4 thyroid glands and 4 islets of Langerhans were negative.

Of the tissues of the gastrointestinal tract, the 3 mucous glands that were investigated, one tongue, two esophagi, 3 samples from the duodenum, 4 gall bladders, 4 liver tissues and 4 pancreas tissues were completely negative. In the colon, the goblet cells stained weakly in the 4 samples that were examined.

Both of the 2 lung tissues that were examined were negative. The tissues of the urogenital tract were completely negative, i.e. 2 kidneys, 2 ureters, 1 testicle, 1 ovary and 4 breast tissues were examined. The lymphatic tissues that were examined, such as spleen (5 samples) and tonsils (1 sample) were also negative.

The skeletal muscle and smooth muscle tissues that were examined, two samples of each, were negative. The blood vessels were also negative. Connective tissue showed a weak reaction.

5) FACS analysis with human peripheral blood cells (PBL) showed that the MAb reacted with ≈10% of the PBL.

6) The avidity, which was determined by solid-phase ELISA using purified GD3 according to the method described by Harlow E. and Lane D. (CSHL, p. 23, 1988), lay in the region of $2.3 \times 10^8$ l/mol.

7) The MAb lyses the GD3-expressing SK-Me128 cell in the presence of human serum (diluted 1:4) as the source of complement down to a MAb concentration of 1 µg/ml. These experiments were carried out in a cytotoxicity test corresponding to that published by Welt, S., Carswell, E. A., Vogel, C.-W., Oettgen, H. F., Old, L. J. (Clin. Immunol. Immunopathol. 45: 214–229, 1987). The ability to bind human complement, and thereby kill tumor cells, is a property which other MAbs of the IgG3 isotype also possess.

The properties of the MAb BW 2121, as described under 1–7, render it superior to the MAbs known from the literature, in particular MAb R24 (Dippold, W. G., Lloyd K. O., Li, L. T. C., Ikeda, H., Oettgen, H. F., Old, L. J., Proc. Natl. Acad. Sci. USA 77: 6144–6148, 1980).

In general, MAb BW 2121 has the following advantages over MAb R24:

1) Less Cross-reaction with Normal Tissue, i.e.: MAb R24 reacts with the medulla of the adrenal glands as well as with the Goormaghtigh cells; It additionally reacts with the epithelial cells in the tonsils and with connective tissue.

2) Greater Avidity

MAbR24 has an avidity of $2 \times 10^7$ l/mol, ≈1 log less than MAb BW 2121.

Improved Cytotoxic Potential

In order to achieve 20% complement-dependent cytolysis of SK-Me128 melanoma cells, 10 µg/ml of MAb R24 are required, whereas 1 µg/ml of MAb BW 2121 has the same effect.

The MAbs according to the invention are therefore particularly suitable for the in vitro or in vivo detection or therapy of tumors which express the epitope recognized by MAb BW 2121, in particular for detecting melanomas and other tumors or tissues expressing GD3 and GQ1b.

The antigen, which can be isolated biochemically, for example, by using extraction with organic solvents such as chloroform-methanol-water mixtures, is particularly suitable for preparing or examining antibodies which are equivalent to MAb BW 2121, or immunologically reactive parts thereof, and for preparing mimetics.

The antibodies according to the invention can be labeled with radioactive isotopes, in particular with Tc-99m (Schwarz, A., Steinstraesser, A., J. Nucl. Med. 28: 721, 1987). Labeling with paramagnetic compounds represents a further possibility.

Additionally, the V genes of the heavy and light chains of MAb BW 2121 can be isolated by the method described by Orlandi, R., Güssow, D., Jones, P. T., Winter, G. (Proc. Natl. Acad. Sci. USA 86: 3833–3837, 1989), and the nucleic acid sequence of the essential regions of the V gene exon can be determined by the method described by Sanger, F., Nicklen, S., Coulson, A. R. (Proc. Natl. Acad. Sci. USA 74: 5463–5467, 1977). The nucleic acid sequences and the corresponding amino acid sequences are presented in Tab. 1a and 1b. The cloned V genes can also be expressed in BHK cells as chimeric MAbs with a truncated human IgG3 Fc moiety (IgG3) and human C-kappa (Wirth, M., Bode, J., Zettlmeissl, G., Hauser, H. Gene 73: 419–426, 1988). Additionally, the mrus (minimal recognition units) can be determined, for example after polypeptide synthesis of the CDRs or of parts of or of several defined CDRs, and employed as specific, only weakly immunogenic peptides for locating tumors in vivo. Additionally, a mimetic with high specificity and avidity towards the epitope defined by MAb BW 2121 can be produced by organic chemical synthesis using the method described by Saragovi, H. U., Fitzpatrick, D., Raktabutr, A., Nakanishi, H., Kahn, M., Greene, M. (Science 253: 792–795, 1991). The murine and humanized V region of MAb BW 2121 can, for example, be linked recombinantly with nucleotide sequences which code for an enzyme or a complement component. These constructs can, when linked at the DNA level, be expressed as functional fusion proteins, as shown in the German Patent Application P41 06 389.9 (Ma 876) for the example of a humanized αCEA MAb and human β-glucuronidase.

TABLE 1a

BW 2121 VR Mouse

1 CAG GTC CAG CTG CAG CAG TCA GGG GGA GGC TTA GTG AAG CCT GGA GGG TCC
1 Gln Val Gln Leu Gln Gln Ser Gly Gly Gly Leu Val Lys Pro Gly Gly Ser
52 CTG ACA CTC TCC TGT GCA GCC TCT AGA TTC ACT TTC AGT ACC TAT GCC ATG
18 Leu Thr Leu Ser Cys Ala Ala Ser Arg Phe Thr Phe Ser Thr Tyr Ala Met
103 TCT TGG GTT CGC CAG ACT CCG GCG AAG AGG CTG GAG TGG GTC CGA TAC ATT
35 Ser Trp Val Arg Gln Thr Pro Ala Lys Arg Leu GLU Trp Val Ala Tyr Ile
154 AGT AGT GGT GGT GCT AGC ACC TAC TAT CGA GAC AGT GTA AAG GGC CGA TTC
52 Ser Ser Gly Gly Ala Ser Thr Tyr Tyr Arg Asp Ser Val Lys Gly Arg Phe
205 ACC ATC TCC AGA GAC AAT GCC AAG AAC ACC CTG TAT TTG CAA ATG AGC AGT
69 Thr Ile Ser Arg Asp Asn Ala Lys Asn Thr Leu Tyr Leu Gln Met Ser Ser
256 CTG AGG TCT GAG GAC ACG GCC ATG TAT TAC TGT GCA AGA GGA GGG TCC AGG
86 Leu Arg Ser Glu Asp Thr Ala Met Tyr Tyr Cys Ala Arg Gly Gly Ser Arg
307 TAT GCT ATG GAC TAT TGG GGC CAA GGG ACC ACG GTC ACC GTC TCC TCA (SEQ ID NO:1)
103 Tyr Ala Met Asp Tyr Trp Gly Gln Gly Thr Thr Val Thr Val Ser Ser (SEQ ID NO:2)

TABLE 1b

BW 2121 VK Mouse

1 GAC ATC CAG CTG ACC CAG TCT CCA GCC ATC CTG TCT GTG AGT CCA GGA GAA
1 Asp Ile Gln Leu Thr Gln Ser Pro Ala Ile Leu Ser Val Ser Pro Gly Glu
52 AGA GTC AGT TTC TCC TGC TGG GCC AGT CAG AGC ATT GGC ACA AGC ATA CAC
18 Arg Val Ser Phe Ser Cys Trp Ala Ser Gln Ser Ile Gly Thr Ser Ile His
103 TGG TAT CAA CAA AGA ACA AAT GGT TCT CCA AGG CTT CTC ATT AAG TAT TCT

TABLE 1b-continued

BW 2121 VK Mouse

```
 35 Trp Tyr Gln Gln Arg Thr Asn Gly Ser Pro Arg Leu Leu Ile Lys Tyr Ser
154 TCT GAG TCT ATC TCT GGG ATC CCT TCC AGG TTT AGT GGC AGT GGA TCA GGG
 52 Ser Glu Ser Ile Ser Gly Ile Pro Ser Arg Phe Ser Gly Ser Gly Ser Gly
205 ACA GAT TTT ACT CTT AGC ATC AAC AGT TTG GAG TCT GAA GAT ATT GCA GAT
 69 Thr Asp Phe Thr Leu Ser Ile Asn Ser Leu Glu Ser Glu Asp Ile Ala Asp
256 TAT TAC TGT CAA CAA ACT TAT AGC TGG CCA TTC ACG TTC GGC TCG GGG ACC
 86 Tyr Tyr Cys Gln Gln Thr Tyr Ser Trp Pro Phe Thr Phe Gly Ser Gly Thr
307 AAG CTG GAG ATC (SEQ ID NO:3)
103 Lys Leu Glu Ile (SEQ ID NO:4)
```

We claim:

1. The monoclonal antibody BW 2121, which is derived from the hybridoma 2121 (DSM ACC 2036).

2. Monoclonal antibodies or parts thereof, which bind to an epitope which is recognized by a monoclonal antibody as claimed in claim 1 and do not react with the medulla of the adrenal glands or the Goormaghtigh cells in immunohistochemical investigations.

3. The monoclonal antibody of claim 1, wherein said antibody is a chimeric antibody.

4. The monoclonal antibody of claim 1, wherein said antibody is a humanized antibody.

5. A pharmaceutical composition containing one or more antibodies as claimed in claim 2 in a therapeutically effective dose and a pharmaceutically acceptable carrier.

6. A process for preparing a monoclonal antibody as claimed in claim 2, wherein immunocompetent mammals are immunized with immunogen containing GD3; GQ1b; or GD3 and GQ1b, and the hybridomas specific for GD3 and GQ1b are isolated.

7. The hybridoma 2121 (DSM ACC 2036).

8. A diagnostic agent containing one or more labelled monoclonal antibodies as claimed in claim 3.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 354 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CAGGTCCAGC TGCAGCAGTC AGGGGGAGGC TTAGTGAAGC CTGGAGGGTC CCTGACACTC      60
TCCTGTGCAG CCTCTAGATT CACTTTCAGT ACCTATGCCA TGTCTTGGGT TCGCCAGACT     120
CCGGCGAAGA GGCTGGAGTG GGTCCGATAC ATTAGTAGTG GTGGTGCTAG CACCTACTAT     180
CGAGACAGTG TAAAGGGCCG ATTCACCATC TCCAGAGACA ATGCCAAGAA CACCCTGTAT     240
TTGCAAATGA GCAGTCTGAG GTCTGAGGAC ACGGCCATGT ATTACTGTGC AAGAGGAGGG     300
TCCAGGTATG CTATGGACTA TTGGGGCCAA GGGACCACGG TCACCGTCTC CTCA           354
```

( 2 ) INFORMATION FOR SEQ ID NO:2:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Gln Val Gln Leu Gln Gln Ser Gly Gly Gly Leu Val Lys Pro Gly Gly
  1               5                  10                  15

Ser Leu Thr Leu Ser Cys Ala Ala Ser Arg Phe Thr Phe Ser Thr Tyr
             20                  25                  30

Ala Met Ser Trp Val Arg Gln Thr Pro Ala Lys Arg Leu Glu Trp Val
         35                  40                  45

Ala Tyr Ile Ser Ser Gly Gly Ala Ser Thr Tyr Tyr Arg Asp Ser Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Met Tyr Tyr Cys
                 85                  90                  95

Ala Arg Gly Gly Ser Arg Tyr Ala Met Asp Tyr Trp Gly Gln Gly Thr
```

```
                        100                          105                           110
        Thr  Val  Thr  Val  Ser  Ser
                       115
```

(2) INFORMATION FOR SEQ ID NO:3:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
GACATCCAGC  TGACCCAGTC  TCCAGCCATC  CTGTCTGTGA  GTCCAGGAGA  AAGAGTCAGT    60
TTCTCCTGCT  GGGCCAGTCA  GAGCATTGGC  ACAAGCATAC  ACTGGTATCA  ACAAAGAACA   120
AATGGTTCTC  CAAGGCTTCT  CATTAAGTAT  TCTTCTGAGT  CTATCTCTGG  GATCCCTTCC   180
AGGTTTAGTG  GCAGTGGATC  AGGGACAGAT  TTTACTCTTA  GCATCAACAG  TTTGGAGTCT   240
GAAGATATTG  CAGATTATTA  CTGTCAACAA  ACTTATAGCT  GGCCATTCAC  GTTCGGCTCG   300
GGGACCAAGC  TGGAGATC                                                    318
```

(2) INFORMATION FOR SEQ ID NO:4:

(i) SEQUENCE CHARACTERISTICS:
        (A) LENGTH: 106 amino acids
        (B) TYPE: amino acid
        (D) TOPOLOGY: linear (ii) MOLECULE TYPE: peptide (xi) SEQUENCE DESCRIPTION: SEQ ID NO:4:

```
Asp  Ile  Gln  Leu  Thr  Gln  Ser  Pro  Ala  Ile  Leu  Ser  Val  Ser  Pro  Gly
 1                  5                        10                       15
Glu  Arg  Val  Ser  Phe  Ser  Cys  Trp  Ala  Ser  Gln  Ser  Ile  Gly  Thr  Ser
               20                       25                       30
Ile  His  Trp  Tyr  Gln  Gln  Arg  Thr  Asn  Gly  Ser  Pro  Arg  Leu  Leu  Ile
          35                        40                       45
Lys  Tyr  Ser  Ser  Glu  Ser  Ile  Ser  Gly  Ile  Pro  Ser  Arg  Phe  Ser  Gly
     50                       55                       60
Ser  Gly  Ser  Gly  Thr  Asp  Phe  Thr  Leu  Ser  Ile  Asn  Ser  Leu  Glu  Ser
65                       70                       75                        80
Glu  Asp  Ile  Ala  Asp  Tyr  Tyr  Cys  Gln  Gln  Thr  Tyr  Ser  Trp  Pro  Phe
                    85                       90                       95
Thr  Phe  Gly  Ser  Gly  Thr  Lys  Leu  Glu  Ile
               100                      105
```